US00PP19475P2

(12) United States Plant Patent
Klemm

(10) Patent No.: US PP19,475 P2
(45) Date of Patent: Nov. 25, 2008

(54) *CALIBRACHOA* PLANT NAMED 'KLECA07108'

(50) Latin Name: ***Calibrachoa* sp.**
Varietal Denomination: KLECA07108

(75) Inventor: Nils Klemm, Stuttgart (DE)

(73) Assignee: Klemm + Sohn GmbH + Co KG, Stuttgart (DE)

( * ) Notice: Subject to any disclaimer, the term of this patent is extended or adjusted under 35 U.S.C. 154(b) by 0 days.

(21) Appl. No.: 12/002,455

(22) Filed: Dec. 17, 2007

(51) Int. Cl.
*A01H 5/00* (2006.01)

(52) U.S. Cl. ..... Plt./413
(58) Field of Classification Search ..... Plt./413
See application file for complete search history.

(56) References Cited

U.S. PATENT DOCUMENTS

PP14,185 P2 * 9/2003 Klemm ..... Plt./413
PP15,567 P2 * 2/2005 Kievit ..... Plt./413
PP15,876 P2 * 7/2005 Westhoff ..... Plt./413

OTHER PUBLICATIONS

UPOV ROM GTITM Computer Database, GTI Jouve Retieval Software 2007/02 Citation for 'KLECA07108'.*

* cited by examiner

*Primary Examiner*—Wendy C. Haas
(74) *Attorney, Agent, or Firm*—C. A. Whealy

(57) ABSTRACT

A new and distinct cultivar of *Calibrachoa* plant named 'KLECA07108', characterized by its trailing growth habit; freely branching habit; freely flowering habit; white-colored flowers; and good garden performance.

1 Drawing Sheet

Botanical designation: *Calibrachoa* sp.
Cultivar denomination: 'KLECA07108'.

BACKGROUND OF THE INVENTION

The present invention relates to a new and distinct cultivar of *Calibrachoa,* botanically known as *Calibrachoa* sp. and hereinafter referred to by the name 'KLECA07108'.

The new *Calibrachoa* is a product of a planned breeding program conducted by the Inventor in Stuttgart, Germany. The objective of the breeding program is to create new freely-branching *Calibrachoa* cultivars with compact and trailing plant habit, early and freely flowering habit, and unique and attractive flower color.

The new *Calibrachoa* originated from an open-pollination during the summer of 2002 in Stuttgart, Germany of a proprietary selection of *Calibrachoa* sp. identified as code number T 105, not patented, as the female, or seed, parent with an unknown proprietary selection of *Calibrachoa* sp., as the male, or pollen, parent. The new *Calibrachoa* was discovered and selected by the Inventor as a single flowering plant within the progeny of the stated open-pollination in a controlled environment in Stuttgart, Germany in May, 2003.

Asexual reproduction of the new *Calibrachoa* by vegetative cuttings in a controlled environment in Stuttgart, Germany since may, 2003, has shown that the unique features of this new *Calibrachoa* are stable and reproduced true to type in successive generations.

SUMMARY OF THE INVENTION

The cultivar KLECA07108 has not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'KLECA07108'. These characteristics in combination distinguish 'KLECA07108' as a new and distinct cultivar of *Calibrachoa:*

1. Trailing growth habit.
2. Freely branching habit.
3. Freely flowering habit.
4. White-colored flowers.
5. Good garden performance.

Plants of the new *Calibrachoa* can be compared to plants of the female parent selection. Plants of the new *Calibrachoa* differ primarily from plants of the female parent selection in growth habit as plants of the female parent selection are more upright than plants of the new *Calibrachoa.*

Plants of the new *Calibrachoa* can be compared to plants of the cultivar KLEC01058, disclosed in U.S. Plant Pat. No. 14,185. In side-by-side comparisons conducted in Stuttgart, Germany, plants of the new *Calibrachoa* differed primarily from plants of the cultivar KLEC01058 in growth habit as plants of the cultivar KLEC01058 were more upright than plants of the new *Calibrachoa.*

BRIEF DESCRIPTION OF THE PHOTOGRAPH

The accompanying colored photograph illustrates the overall appearance of the new *Calibrachoa,* showing the colors as true as it is reasonably possible to obtain in colored reproductions of this type. Colors in the photograph may differ slightly from the color values cited in the detailed botanical description which accurately describe the colors of the new *Calibrachoa.* The photograph comprises a side perspective view of a typical flowering plant of 'KLECA07108' grown in a hanging basket container.

DETAILED BOTANICAL DESCRIPTION

The aforementioned photograph and following observations, measurements and values describe plants grown in Stuttgart, Germany, under commercial practice during the spring in a glass-covered greenhouse with day and night temperatures ranging from 14° C. to 16° C. and light levels averaging 20,000 lux. Rooted young plants had been growing for about six months when the photograph and description were taken. Plants used for the description were grown in 12-cm containers and pinched one time one week after planting. In the following description, color references are made to The Royal Horticultural Society Colour Chart, 1995 Edition, except where general terms of ordinary dictionary significance are used.

Botanical classification: *Calibrachoa* sp. cultivar KLECA07108.

Parentage:

*Female, or seed, parent.*—Proprietary selection of *Calibrachoa* sp. identified as code number T 105, not patented.

*Male, or pollen, parent.*—Unknown proprietary selection of *Calibrachoa* sp., not patented.

Propagation:

*Type.*—By vegetative cuttings.

*Time to produce a rooted young plant, summer.*—About three weeks at temperatures of 20° C. to 26° C.

*Time to produce a rooted young plant, winter.*—About four weeks at temperatures of 20° C.

*Root description.*—Fine, fibrous; white in color.

*Rooting habit.*—Freely branching; moderately dense.

Plant description:

*Plant and growth habit.*—Trailing growth habit; vigorous. Freely branching habit with about five to six primary lateral branches each with multiple secondary lateral branches; pinching is typically not required.

*Plant height.*—About 3 cm.

*Plant diameter.*—About 24 cm.

Lateral branch description:

*Length.*—About 12 cm.

*Diameter.*—About 2 mm.

*Internode length.*—About 0.5 cm to 2 cm.

*Strength.*—Strong.

*Aspect.*—Mostly upright.

*Texture.*—Smooth, glabrous.

*Color.*—145A.

Foliage description:

*Arrangement.*—Alternate, simple; sessile.

*Length.*—About 1 cm to 2 cm.

*Width.*—About 0.5 cm to 1 cm.

*Shape.*—Lanceolate to elliptical.

*Apex.*—Broadly acute.

*Base.*—Attenuate.

*Margin.*—Entire.

*Texture, upper and lower surfaces.*—Smooth, glabrous.

*Venation pattern.*—Pinnate; arcuate.

*Color.*—Developing and fully expanded foliage, upper surface: 137A; venation, 144A. Developing and fully expanded foliage, lower surface: 137C; venation, 144B.

Flower description:

*Flower arrangement and habit.*—Salverform flowers arranged singly arising from leaf axils. Freely flowering habit with usually about 54 open flowers and flower buds developing per lateral branch. Flowers not persistent. Flowers face mostly outwardly.

*Fragrance.*—None detected.

*Natural flowering season.*—Plants flower continuously throughout the summer in Germany. Plants begin flowering about 13 weeks after planting.

*Flower longevity.*—Individual flowers last about one week on the plant.

*Flower diameter.*—About 2.7 cm.

*Flower length (height).*—About 1.5 cm.

*Flower throat diameter.*—About 6 mm.

*Flower tube diameter, base.*—About 2 mm.

*Flower tube length.*—About 1.5 cm.

*Flower bud.*—Shape: Elongated oblong. Length: About 2 cm. Diameter: About 5 mm. Color: 154C.

*Corolla.*—Arrangement: Five petals fused at the base and opening into a flared trumpet. Petal length from throat: About 1.3 cm. Petal lobe width: About 1.2 cm. Petal shape: Obverse. Petal apex: Obtuse. Petal margin: Entire. Petal texture, upper and lower surfaces: Smooth, glabrous; satiny. Throat and tube texture: Smooth, glabrous. Color: Petal, when opening and fully opened, upper surface: 155B; color becoming closer to 155A with development; venation, 160B. Petal, when opening and fully opened, lower surface: 155A; venation, 151C. Throat: 155B; venation, 160B. Tube: 5A; venation, 160B.

*Calyx.*—Arrangement: One star-shaped calyx tube with five sepals fused at the base per flower. Sepal length: About 1.2 cm. Sepal width: About 2 mm. Sepal shape: Lanceolate to elliptical. Sepal apex: Acute. Sepal margin: Entire. Sepal texture, upper and lower surfaces: Smooth, glabrous. Color, upper surface: 138A. Color, lower surface: 138B.

*Peduncles.*—Length: About 2 cm. Diameter: About 2 mm. Angle: Erect to about 65° from stem axis. Strength: Moderately strong. Texture: Smooth, glabrous. Color: 144B.

*Reproductive organs.*—Stamens: Quantity/arrangement: Five per flower. Anther shape: Elliptic. Anther length: About 1 mm. Anther color: 11A. Pollen amount: Moderate. Pollen color: 11A. Pistils: Quantity: One per flower. Pistil length: About 5 mm. Style length: About 2 mm. Style color: 150A. Stigma shape: Oval. Stigma color: 149A. Ovary color: 154A. Seed/fruit: Seed and fruit development have not been observed on plants of the new *Calibrachoa*.

Garden performance: Plants of the new *Calibrachoa* have been observed to have good garden performance and tolerate wind, rain and temperatures ranging from about 1° C. to about 50° C.

Pathogen/pest resistance: Plants of the new *Calibrachoa* have not been observed to be resistant to pathogens and pests common to *Calibrachoa*.

It is claimed:

1. A new and distinct *Calibrachoa* plant named 'KLECA07108' as illustrated and described.

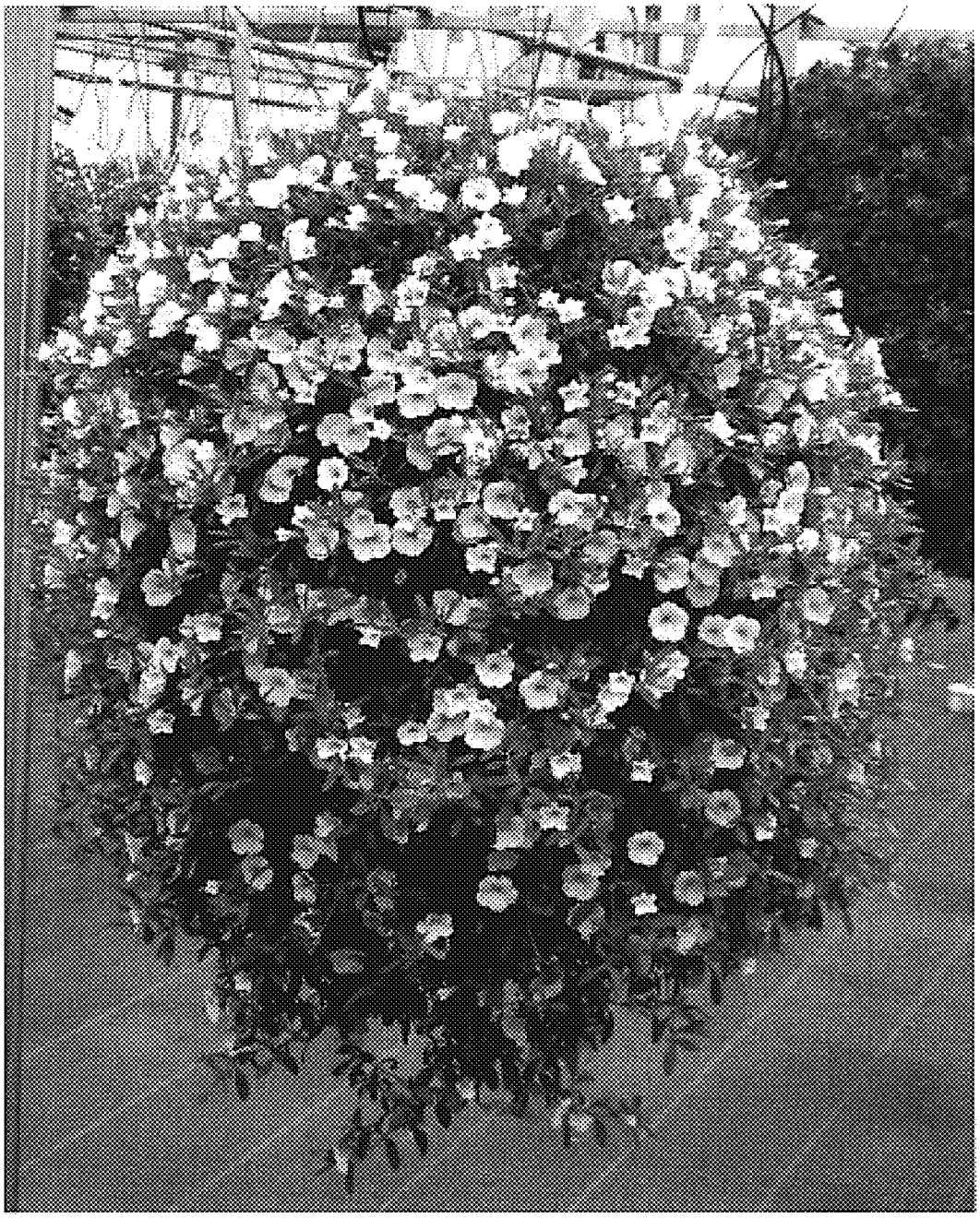

* * * * *